United States Patent
Lee et al.

(10) Patent No.: US 7,391,225 B1
(45) Date of Patent: Jun. 24, 2008

(54) CARBON NANOTUBE SENSOR AND APPARATUS AND METHOD FOR DETECTING CHANGE TIME OF ENGINE OIL FOR AUTOMOBILE USING THE SAME

(75) Inventors: Min Ho Lee, Gyeonggi-Do (KR); Dae Suk Na, Daegu (KR)

(73) Assignee: ST&I, Co., Ltd., Gyeonggi-do (KR)

( * ) Notice: Subject to any disclaimer, the term of this patent is extended or adjusted under 35 U.S.C. 154(b) by 0 days.

(21) Appl. No.: 11/402,321

(22) Filed: Apr. 11, 2006

(30) Foreign Application Priority Data

Apr. 13, 2005 (KR) .................... 10-2005-0030804
Oct. 27, 2005 (KR) .................... 10-2005-0101716

(51) Int. Cl.
*G01R 27/08* (2006.01)

(52) U.S. Cl. ...................... 324/698; 436/151
(58) Field of Classification Search ............... 324/698; 436/151
See application file for complete search history.

(56) References Cited

U.S. PATENT DOCUMENTS

| | | | |
|---|---|---|---|
| 4,971,583 A * | 11/1990 | Umehara | 440/2 |
| 6,278,281 B1 * | 8/2001 | Bauer et al. | 324/441 |
| 6,580,366 B1 * | 6/2003 | Engfehr | 340/457.4 |
| 7,013,708 B1 * | 3/2006 | Cho et al. | 73/31.05 |
| 2006/0253942 A1 * | 11/2006 | Barrera et al. | 977/852 |

* cited by examiner

*Primary Examiner*—Andrew H. Hirshfeld
(74) *Attorney, Agent, or Firm*—Harness, Dickey & Pierce, PLC

(57) ABSTRACT

A system and method for determining the time to change the oil of an automobile engine including a power source unit for converting power into necessary power and supplies power at the startup time. A degradation detection unit is installed in an engine oil chamber and is formed using carbon nanotubes as a sensor capable of detecting degradation of the engine oil. A small signal amplification unit amplifies the signals detected from the oil conditions and amplifies the minute signal output from the degradation detection unit. The oil-condition determination unit compares value, corresponding to the degraded state of the engine oil, with a set reference value, to determine the time to change the engine oil. The display unit displaying the oil-condition in text form as information about the time to change oil.

9 Claims, 8 Drawing Sheets

CARBON NANOTUBE SENSOR AND APPARATUS AND METHOD FOR DETECTING CHANGE TIME OF ENGINE OIL FOR AUTOMOBILE USING THE SAME

BACKGROUND OF THE INVENTION

1. Field of the Invention

The present invention relates generally to an apparatus and method for determining the time to change automobile engine oil and, more particularly, to an apparatus and method for determining the time to change automobile engine oil, which measure variation in permittivity or electric conductivity of engine oil using a sensor having carbon nanotubes and determine and indicate the time to change the engine oil.

2. Description of the Related Art

Generally, engine oil, which is loaded in an automobile, performs a lubricating function of maintaining the smooth reciprocating motion of a piston, which is performed in response to an explosion in an engine, a sealing function of preventing pressure from leaking, a cleaning function of adsorbing particles in the cylinder and preventing the inner wall of a cylinder from being damaged, and a cooling function of conducting heat away from the cylinder and the piston.

When the engine oil, having the above-described functions, is used for a long time, the amount of injected oil decreases due to combustion by the explosions, and the viscosity, total acid number, and amount of sludge contained in the engine oil vary due to degradation.

Accordingly, the engine oil must be changed periodically. In the case where the time to change engine oil is missed or the operation of an automobile continues without changing the oil, the durability of lubricated parts in an engine requiring lubrication is lowered, the lifespan is reduced, the payment of excessive repair cost are incurred, and the excessive consumption of fuel, attributable to decreased engine output, and environmental problems, attributable to the increase of exhaust gas, also result.

Accordingly, periodical checks must be performed on the engine oil, and the change time must be determined according to the condition of the engine oil. For these purposes, a driver determines the time to change the engine oil based on the driven distance indicated on an integrated meter in a cluster mounted on an instrument panel, or determines the time to change the engine oil by observing a dipstick, which is provided in an engine compartment, with the naked eye, measuring the amount of engine oil, and viscosity and color thereof, and determining the extent of the degradation of the engine oil.

As described above, the conventional method of determining the time to change engine oil is disadvantageous in that it is inconvenient for a driver to personally calculate the driven distance and to personally check the extent of the degradation of the engine oil.

Furthermore, the extent of the degradation of the engine oil is determined through the driver's subjective observation and is thus inaccurate. Accordingly, a disadvantage occurs in that waste and environmental pollution result from unnecessary engine oil changes, and the wear of respective lubricated parts within an engine results from excessively late changes, so that the durability thereof is lowered.

Furthermore, a disadvantage occurs in that the extent of the degradation of the engine oil varies according to the driver's driving habits, so that the actual change time differs from that recommended in a maintenance guide book, therefore it is difficult to determine the change time.

In order to solve the above-described disadvantages incurred by determining the time to change the engine oil by using the naked eye to observe variation in viscosity and color, a technology has been proposed in Korean Pat. Appl. No. 1997-54022, that, when the change times of respective consumable supplies for an automobile are set based on a driving distance and then an accumulated driving distance reaches the set driving distance, alarms at the driver of the time to change the consumable supplies, such as engine oil, brake oil, an air filter, and brake disks.

Furthermore, Korean Pat. Appl. No. 1996-63422 proposed a technology that passes near infrared rays through oil and determines the time to change the oil based on the level of the received rays.

However, in the former case, the time to change the respective consumable supplies provided in an automobile is based on an accumulated driving distance, so that, for the respective consumable supplies, and particularly for engine oil, considerable difference in the extent of the degradation thereof occurs due to variation in drivers' driving habits, unnecessary idling, or other reasons. Accordingly, the former case is disadvantageous in that it is inaccurate, so that the engine oil is not changed at the proper time, therefore economic waste is incurred and the durability of the engine is lowered.

Furthermore, the latter case is disadvantageous in that the time to change the oil cannot be detected if a near infrared ray radiating or receiving element is damaged, normal determination of the change time cannot be performed in the state in which the amount of oil is low, the change time cannot be accurately detected because the degree of transparency of oil is different for each manufacturing company, which thereby decreases the reliability of detection.

Furthermore, since the degradation of engine oil occurs due to variation according to numerous physical and chemical aspects, the method of determining the time to change the engine oil simply by measuring variation in viscosity or color is limited.

Meanwhile, recently, as the fact that the extent of degradation of engine oil is closely related to variation in permittivity and electric conductivity, which are electric characteristics of the engine oil, become known, research into methods of detecting the condition of engine oil by measuring the electrical characteristics of the engine oil is being conducted.

Meanwhile, although a method of using output voltage, Alternating Current (AC) impedance, and viscosity is employed by foreign companies, the commercialization of resulting products has been delayed because the method seems to have some problems.

Meanwhile, measuring variation in electric conductivity or permittivity, which is caused by various physical and chemical variations in engine oil, is advantageous in that it allows information about variation in engine oil to be easily acquired.

However, until now, measuring apparatuses using electric conductivity or permittivity have a cylinder or parallel plate form that is voluminous, therefore are disadvantageous because they are not compact and mass-produced.

SUMMARY OF THE INVENTION

Accordingly, the present invention has been made keeping in mind the above problems occurring in the prior art, and an object of the present invention is to provide a sensor using carbon nanotubes to detect variation in permittivity and electric conductivity of automobile engine oil, and the manufacturing method thereof.

Furthermore, another object of the present invention is to provide an apparatus and method for determining the time to change automobile engine oil using a sensor having carbon nanotubes, which can measure the extent of the degradation of engine oil to determine the time to change the engine oil and can indicate the time to change the engine oil to a driver.

In order to accomplish the above object, the present invention provides an electric conductivity sensor, including electrodes to which power is applied; a detection film which is connected to both the electrodes and is formed of carbon nanotubes capable of detecting variation in electric conductivity; and a substrate on which the electrodes and the detection film are mounted.

Furthermore, it is preferred that the electrodes be formed of carbon nanotubes.

In addition, the present invention provides a permittivity sensor, including electrodes to which power is applied; a detection film which is connected to both the electrodes and is formed of carbon nanotubes capable of detecting variation in permittivity; and a substrate on which the electrodes and the detection film are mounted.

Furthermore, in the permittivity sensor, it is preferred that the electrodes be formed of carbon nanotubes.

Furthermore, in the permittivity sensor, it is preferred that each of the electrodes or the detection film be branched in a comb-tooth pattern.

Furthermore, in the permittivity sensor, it is preferred that the detection film formed of the carbon nanotubes be deposited or printed on the substrate and allow sensitivity to be controlled according to variation of an area thereof.

In addition, the present invention provides a method of manufacturing a sensor having a carbon nanotube detection film, including the lithography step of coating, exposing, and etching a photoresist on a substrate; the step of patterning electrodes on the substrate using a catalyst; and the step of growing carbon nanotubes on the substrate.

In addition, the present invention provides a method of manufacturing a sensor having a carbon nanotube detection film, including the lithography step of coating, exposing, and etching a photoresist on a substrate; the step of mixing a binder, α-terpineol, carbon nanotubes, and glass frit; and the step of printing the mixed material on the substrate using a screen-printing method and sintering the printed mixed material.

In addition, the present invention provides an apparatus for determining the time to change automobile engine oil, including a power source unit for converting power, which is supplied to a battery, into necessary power and supplying the necessary power at a startup time; a degradation detection unit installed in an engine oil chamber and formed using carbon nanotubes as a sensor capable of detecting degradation of the engine oil; a drive unit for driving the operation of the degradation detection unit when enabled by power supplied from the power source unit; a small signal amplification unit for amplifying a minute signal output from the degradation detection unit; an oil-condition determination unit for comparing a value, corresponding to the degraded state of the engine oil, with a set reference value based on a detection signal transferred from the small signal amplification unit, and thereby determining the time to change the engine oil; an amplification unit for amplifying a signal detected by the oil-condition determination unit to a preset level; and a display unit for displaying a signal, which is output from the oil-condition determination unit, in text or predetermined form as information about an oil change time.

Furthermore, in the apparatus for determining the time to change automobile engine oil, it is preferred that the sensor of the degradation detection unit is an electric conductivity sensor, the electric conductivity sensor including electrodes to which power is applied; a detection film which is connected to both the electrodes and is formed of carbon nanotubes capable of detecting variation in electric conductivity; and a substrate on which the electrode and the detection film are mounted.

Furthermore, in the apparatus for determining the time to change automobile engine oil, it is preferred that the detection film be formed of carbon nanotubes.

Furthermore, in the apparatus for determining the time to change automobile engine oil, it is preferred that the sensor of the degradation detection unit is an electric conductivity sensor, the electric conductivity sensor including electrodes to which power is applied; a detection film which is connected to both the electrodes and is formed of carbon nanotubes capable of detecting variation in permittivity; and a substrate on which the electrodes and the detection film are mounted.

Furthermore, in the apparatus for determining the time to change automobile engine oil, it is preferred that the detection film be formed of carbon nanotubes.

Furthermore, in the apparatus for determining the time to change automobile engine oil, it is preferred each of the electrodes and the detection film be branched in a comb-tooth pattern.

Furthermore, in the apparatus for determining the time to change automobile engine oil, it is preferred a sensitivity of the degradation detection unit varies according to variation in a deposition area of the carbon nanotubes that cover both the electrodes and a predetermined region of an entire area of the substrate.

Furthermore, in the apparatus for determining the time to change automobile engine oil, it is preferred that the power source unit include a DC/DC converter for converting DC power, which is supplied to the battery, into power required by respective loads; and a regulator for stabilizing the power converted by the DC/DC converter.

Furthermore, in the apparatus for determining the time to change automobile engine oil, it is preferred that the display unit include a Light Emitting Diode (LED) or Liquid Crystal Display (LCD) device in a cluster.

Furthermore, in the apparatus for determining the time to change automobile engine oil, it is preferred that the display unit further include an audio speaker for issuing information about oil change time in alarm sound or voice message form.

Furthermore, in the apparatus for determining the time to change automobile engine oil, it is preferred a voltage device of the power source unit further include a thermal sensor so that power can be applied in a temperature range above 80° C.

Furthermore, in the apparatus for determining the time to change automobile engine oil, it is preferred that a power source frequency applied by the drive unit be within a range from 10 kHz to 10 GHz.

In addition, the present invention provides a method for determining the time to change automobile engine oil, including the steps of: supplying power to respective loads when an engine is started; a degradation detection unit, which is installed in an engine oil chamber, measuring variation in permittivity or electric conductivity of the engine oil, and setting a measured value as an initial reference value; an oil-condition determination unit comparing a measured value with the set initial reference value and determining whether an oil change time has been reached when the degradation detection unit measures the extent of the degradation of the engine oil and detects the variation in permittivity or electric conductivity; and the oil-condition determination determining that the engine oil is in a normal condition if a value, corresponding to the variation in permittivity or electric conductivity attributable to the degradation of the engine oil, which is measured by the degradation detection unit, is less than the set reference value, and determining that the time to change the engine oil is reached if the value is equal to or greater than the reference value, and a display means then indicating the time to change the engine oil.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Preferred embodiments of the present invention are described in detail with reference to the accompanying drawings below.

Figure 1:
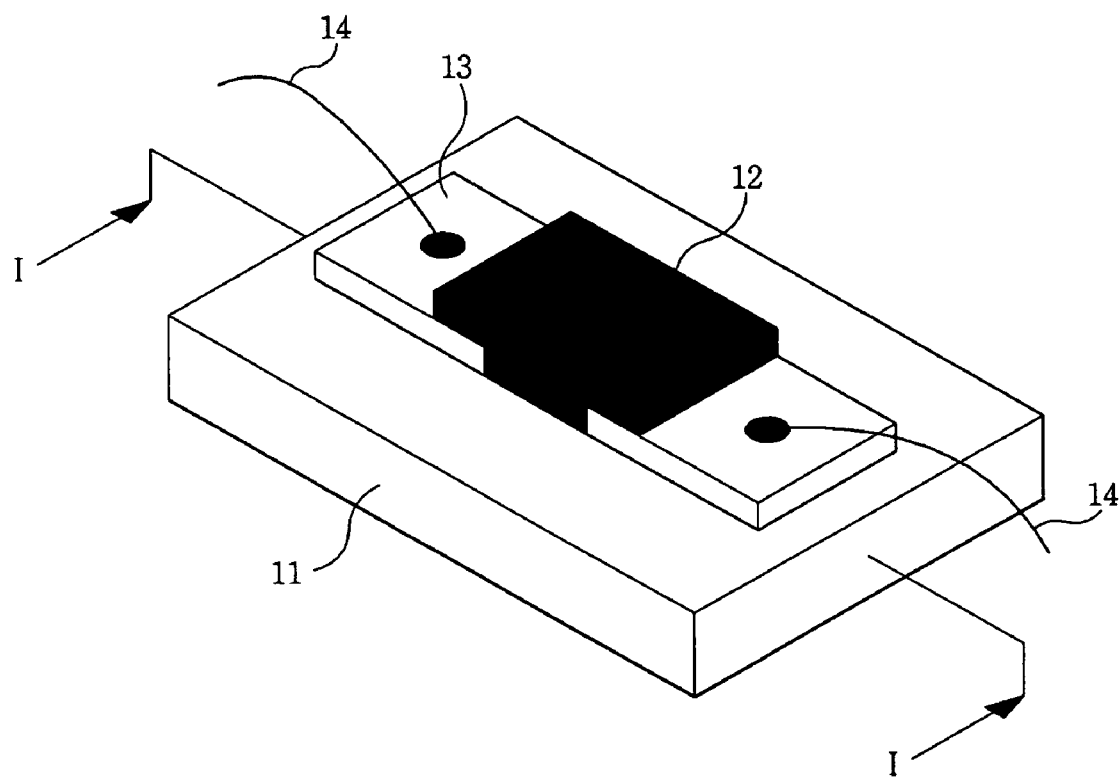
FIG. 1 is a perspective view of an electric conductivity sensor using carbon nanotubes according to the present invention.
Figure 2:
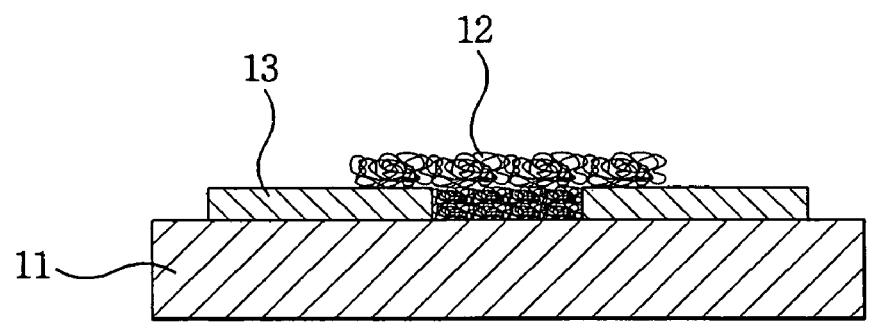
FIG. 2 is a sectional view taken along line I-I of FIG. 1.

FIG. 1 is a perspective view of an electric conductivity sensor using carbon nanotubes according to the present invention, and FIG. 2 is a sectional view taken along line I-I of FIG. 1.

Referring to FIGS. 1 and 2, an electric conductivity sensor using carbon nanotubes according to the present invention includes electrodes 13 to which power is applied, a detection film 12 which is connected to both the electrodes and is formed of carbon nanotubes capable of detecting variation in electric conductivity, and a substrate 11 on which the electrodes 13 and the detection film 12 are mounted.

In this case, the substrate 11 of the sensor is made of glass or silicon.

The carbon nanotubes, which are deposited and grown on the substrate 11 or are formed using a screen printing method, function as the detection film 12, and the detection film 12 is connected to both electrodes 13 to play the role of a bridge.

Furthermore, the electrodes 13 are connected to a power source via lead wires 14, and the lead wires 14 are attached to the electrodes 13 to form a complete closed-loop circuit.

Each the electrodes 13 may be made of Indium Tin Oxide (ITO) or metal, and it may be possible to form the electrodes using carbon nanotubes, like the detection film 12.

The carbon nanotubes, which are connected so as to function as the detection film 12, may be deposited using a semiconductor process and screen printing technology, or using a direct growth method.

Each of the carbon nanotubes has an $sp^2$-bonded tube shape, in which graphite is rolled in a circular fashion, so that the surface area thereof per unit area is very large, therefore the ability to adsorb gas molecules or ions thereon is excellent.

Furthermore, each of the carbon nanotubes has an electrical characteristic like that of a metal or a semiconductor, and has a characteristic in which the electric conductivity thereof varies according to the adsorption of gas molecules or ions thereon.

Accordingly, when Direct Current (DC) voltage is applied in the case where the detection film 12 is formed of the carbon nanotubes, the electric resistance of the detection film 12 varies according to variation in the number of ions adsorbed on the carbon nanotubes, so that variation in electric conductivity can be detected.

Figure 3:
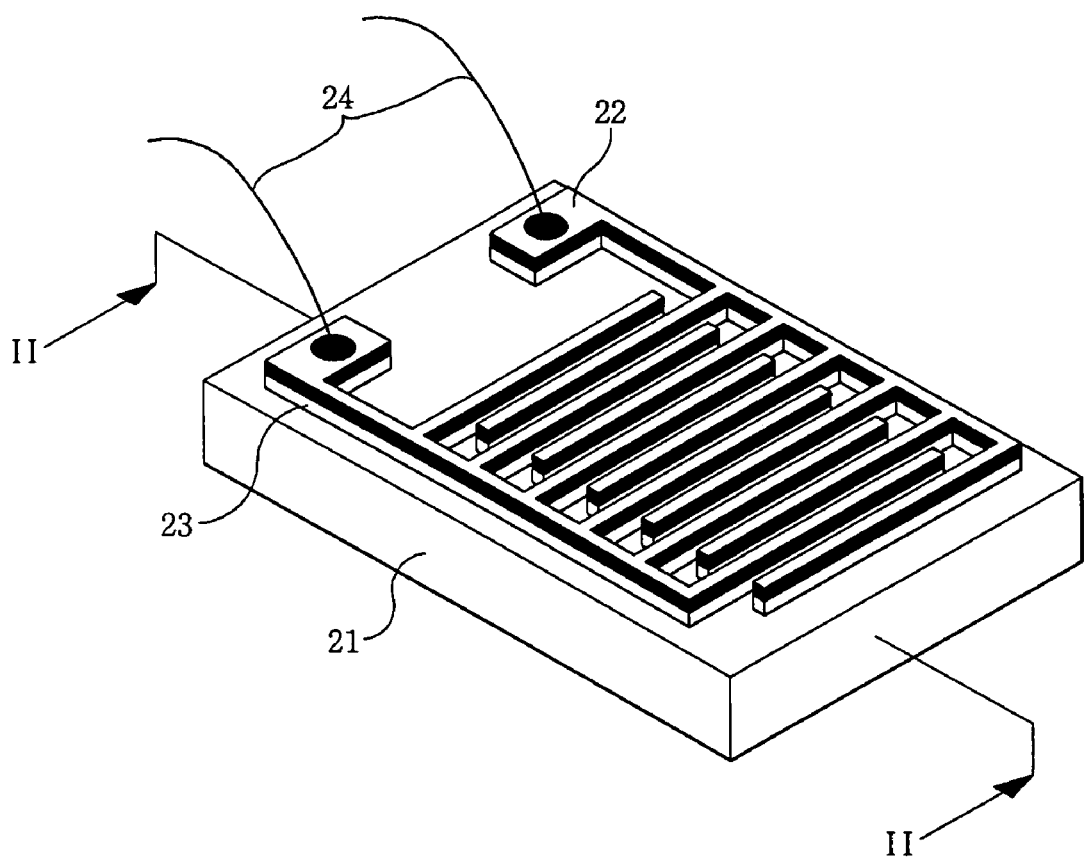
FIG. 3 is a view schematically showing a permittivity sensor using carbon nanotubes according to an embodiment of the present invention.
Figure 4:
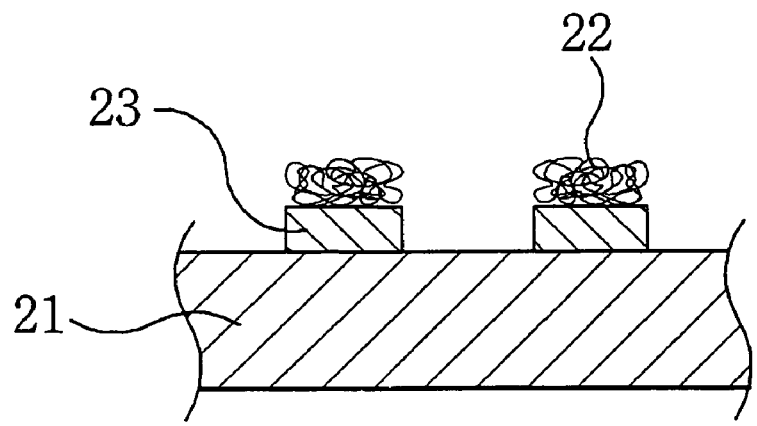
FIG. 4 is a sectional view taken along line II-II of FIG. 3.

Meanwhile, in another embodiment of the carbon nanotube sensor according to the present invention, a description of a permittivity sensor using carbon nanotubes is made with reference to FIGS. 3 and 4.

FIG. 3 is a view schematically showing a permittivity sensor using carbon nanotubes according to an embodiment of the present invention, and FIG. 4 is a sectional view taken along line II-II of FIG. 3.

The permittivity sensor using carbon nanotubes includes electrodes 23 to which power is applied, a detection film 22 which is connected to the electrodes and is formed of carbon nanotubes capable of detecting variation in permittivity, and a substrate 21 on which the electrodes 23 and the detection film 22 are mounted.

Referring to FIG. 4, although, in the permittivity sensor, carbon nanotubes are deposited and screen-printed on the electrodes 23, each of which is made of metal or ITO, it is also possible to form the electrodes 23 from carbon nanotubes.

When voltage is applied, the carbon nanotubes functioning as the detection film undergo variation in capacitance according to variation in the number of ions adsorbed on the carbon nanotubes, thus detecting variation in permittivity.

Furthermore, referring to FIG. 3, in the permittivity sensor, it is preferred that each of the electrodes 23 be branched in a comb-tooth pattern. In this case, the carbon nanotubes that function as the detection film 22 are deposited on the electrodes 23, so that the surface area of the electrodes for the measurement of capacitance is increased, therefore the measuring sensitivity thereof can be largely improved.

In FIG. 3, the detection film may be formed using a method of screen-printing or directly growing carbon nanotubes on base electrodes, each of which has a comb-tooth electrode shape, and which are formed using a photolithography process.

In the sensor, it is appropriate that, when a screen-printing method is used to measure variation in permittivity, the width of each comb-tooth electrode is less than 100 μm, and the gap between the electrodes is less than 100 μm, and it is appropriate that, when a direct growth method is used, the gap between the electrodes is less than 50 μm.

Furthermore, the carbon nanotubes used as the detection film 22 of the sensor are advantageous in that the size thereof is small, they have functions of adsorbing and storing ions, and the surface area thereof per unit area is large, so that the physical and chemical durability is excellent while the sensitivity on a unit basis is high and the response speed is fast.

Furthermore, in the detection sensor using the carbon nanotubes as the detection film 22, many electrodes are formed in a small area using micromachining technology, so that a high-sensitivity sensor can be manufactured and the sensor can conform to uniform standards.

Figure 5:
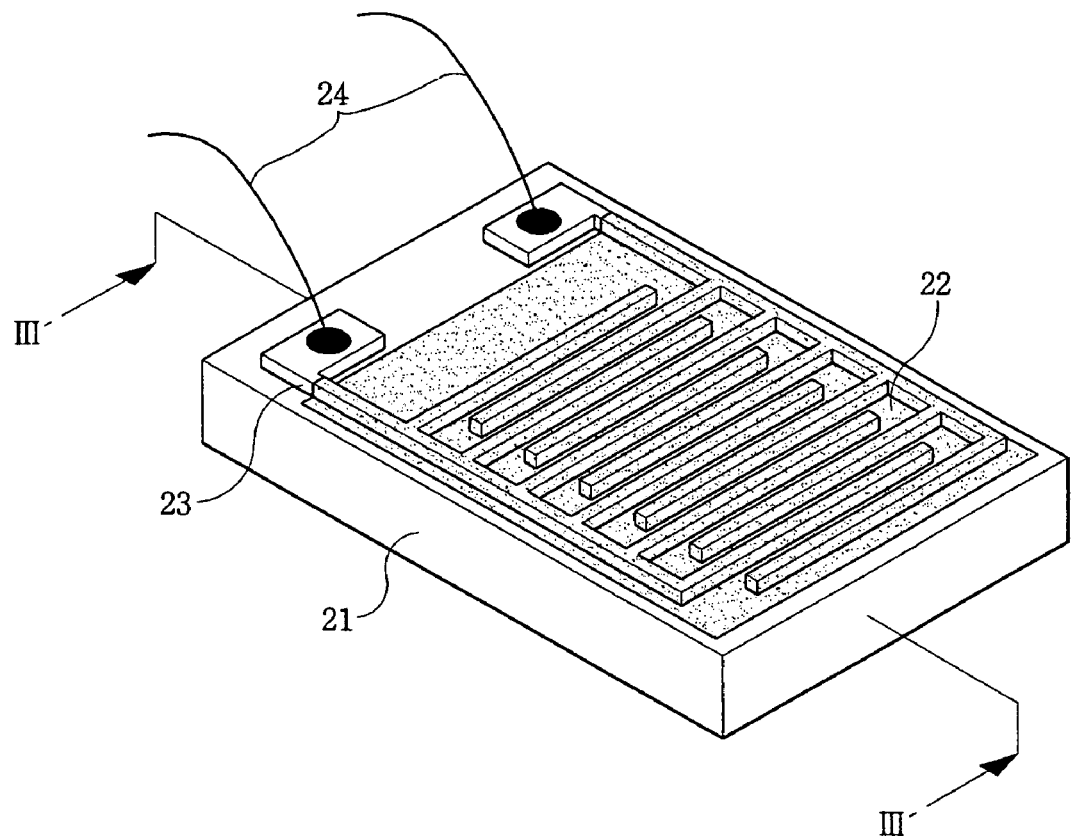
FIG. 5 is a perspective view of a permittivity sensor using carbon nanotubes according to another embodiment of the present invention.
Figure 6:
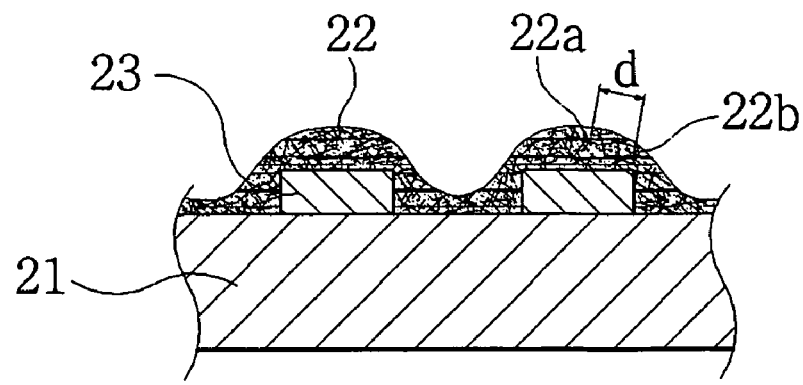
FIG. 6 is a sectional view taken along line III-III of FIG. 5.

FIG. 5 is a perspective view of a permittivity sensor using carbon nanotubes according to another embodiment of the present invention carbon, and FIG. 6 is a sectional view taken along line III-III of FIG. 5. The sensor shown in FIGS. 3 and 4 includes an electrode pattern 23 to which power is applied, a substrate 21 on which the electrode pattern 23 is formed, and a detection film 23 which is formed to cover the electrode pattern 23 and is formed using carbon nanotubes deposited on a predetermine portion of the entire area of the substrate 21.

The carbon nanotubes shown in FIGS. 3 and 4, which function as the detection film, are deposited only on the electrode 23, whereas the detection film shown in FIGS. 5 and 6, that is, the carbon nanotube paste, is formed to cover both the entire electrode pattern 23 and a predetermined region of the substrate 21.

Referring to FIG. 5, it can be seen that the carbon nanotube particles 22a, 22b form the detection film 22, and are deposited on the substrate between the electrodes 23 as well as on the electrodes 23.

FIGS. 5 and 6, when voltage is applied, the carbon nanotubes, functioning as the detection film 22, vary in capacitance according to variation in the number of ions adsorbed on the carbon nanotubes, thus enabling detection of variation in permittivity.

In this case, when various spacing distances 'd' are formed between the carbon nanotube particles 22a and 22b of the detection film 22, minute capacitance exists between a carbon nanotube particle 22a and a neighboring carbon nanotube particle 22b have.

There are numerous carbon nanotube particles adjacent to the single carbon nanotube particle 22a besides the carbon nanotube particle 22b, and the capacitance based on the single carbon nanotube particle 22a is defined as the sum of minute capacitance values generated between the particle 22a and the numerous particles adjacent to the particle 22a.

Meanwhile, when a description is made based on the carbon nanotube particle 22b, a different set of numerous particles, including the carbon nanotube particle 22a, is adjacent to the nanotube particle 22b, so that the capacitance based on the carbon nanotube particle 22b is defined as the sum of minute capacitance values generated between the carbon nanotube particle 22b and the particles adjacent to the carbon nanotube particle 22b.

Accordingly, the total capacitance value detected by the detection film, that is, the total of the minute capacitance values occurring in all of the carbon nanotube particles is defined as a value obtained through summation of the sums.

Figure 7:
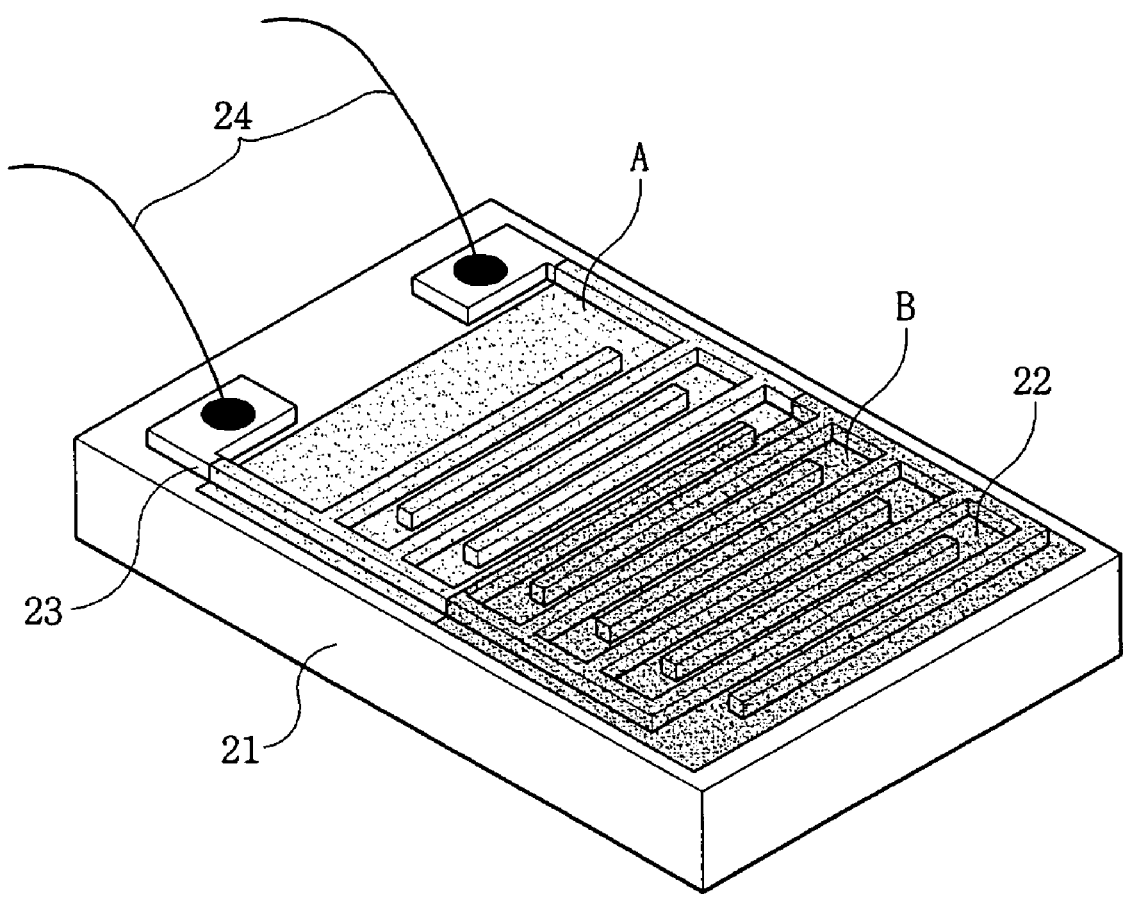
FIG. 7 is a view schematically showing a detection region in the permittivity sensor according to a further embodiment of the present invention.

Meanwhile, FIG. 7 is a view schematically showing a detection region in the permittivity sensor according to a further embodiment of the present invention.

Referring to FIG. 7, when it is desired to vary the initial capacitance value in order to adjust the detection sensitivity of the sensor, the area on which the carbon nanotube paste is printed may be varied.

That is, as shown in FIG. 7, regions 'A' and 'B' indicate regions in which the carbon nanotube paste is printed on the substrate 21, and region 'A' is larger than region 'B'.

A detection film forming region 'A' includes a relatively large number of carbon nanotube particles compared to a detection film forming region 'B', so that the total capacitance value in the case where carbon nanotube paste is deposited on region 'A' is greater than that in the case where second carbon nanotube paste is deposited on region 'B', therefore the initial capacitance value is also larger.

Accordingly, when the deposition area of the carbon nanotube pastes varies, the initial capacitance value can be adjusted, so that the detection sensitivity of the permittivity sensor can be thereby controlled.

The initial capacitance value is important in that variation in floating capacitance acts as a disturbance due to water contained in engine oil, that is, a target to be measured, or due to impurities caused by other factors so that, the initial capacitance value must be more than 400 pF, which was proposed in U.S. Pat. No. 4,646,070, in order to achieve sensitivity such that variation in the capacitance value of the target to be measured can be detected.

Meanwhile, the electric conductivity sensor and the permittivity sensor, which are manufactured by depositing the carbon nanotubes, can be manufactured using new processes instead of existing manufacturing methods.

As a first method, a process of manufacturing a carbon nanotube sensor using semiconductor processing technology is as follows:

First, the lithography step of coating, exposing, and etching a photoresist on a substrate is performed.

Second, the step of performing patterning electrodes on the substrate using a catalyst such as methane gas is performed.

Third, it is preferred that the step of patterning electrodes on the substrate and the step of growing carbon nanotubes on the substrate be sequentially performed.

As second method, a process of manufacturing a carbon nanotube sensor using screen printing technology is as follows:

First, the lithography step of coating, exposing, and etching a photoresist on a substrate is performed.

Second, the step of mixing binder with a-terpineol and heating and melting them is performed.

Third, the step of mixing carbon nanotubes with material obtained by mixing glass frit with a-terpineol and heating and melting them is performed.

Fourth, it is preferred that the step of patterning electrodes on the substrate and the step of printing carbon nanotubes on the substrate using a screen printing method and then sintering the printed carbon nanotubes be sequentially performed.

An apparatus and method for determining the time to change automobile engine oil using the carbon nanotube sensor according to the present invention is now described.

Figure 8:
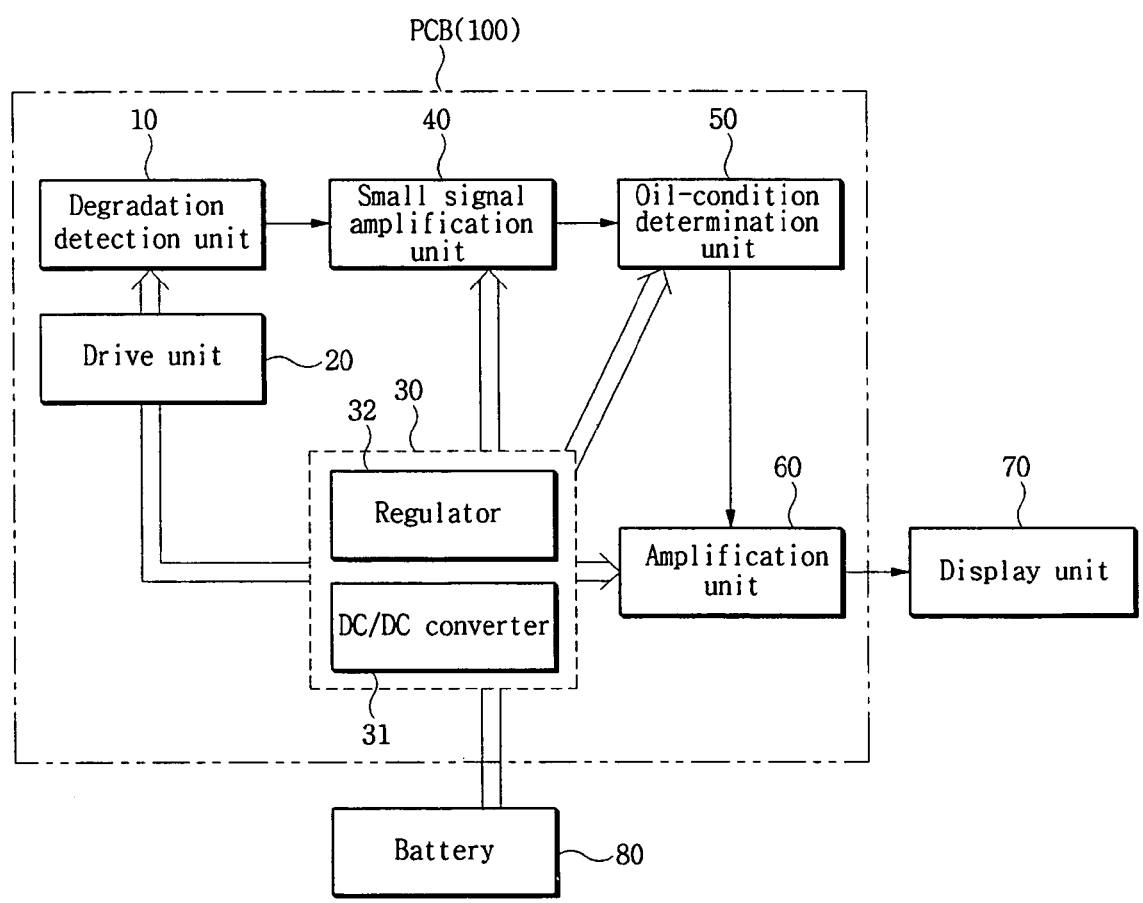
FIG. 8 is a block diagram schematically showing the construction of an apparatus for determining the time to change automobile engine oil according to the present invention.
Figure 9:
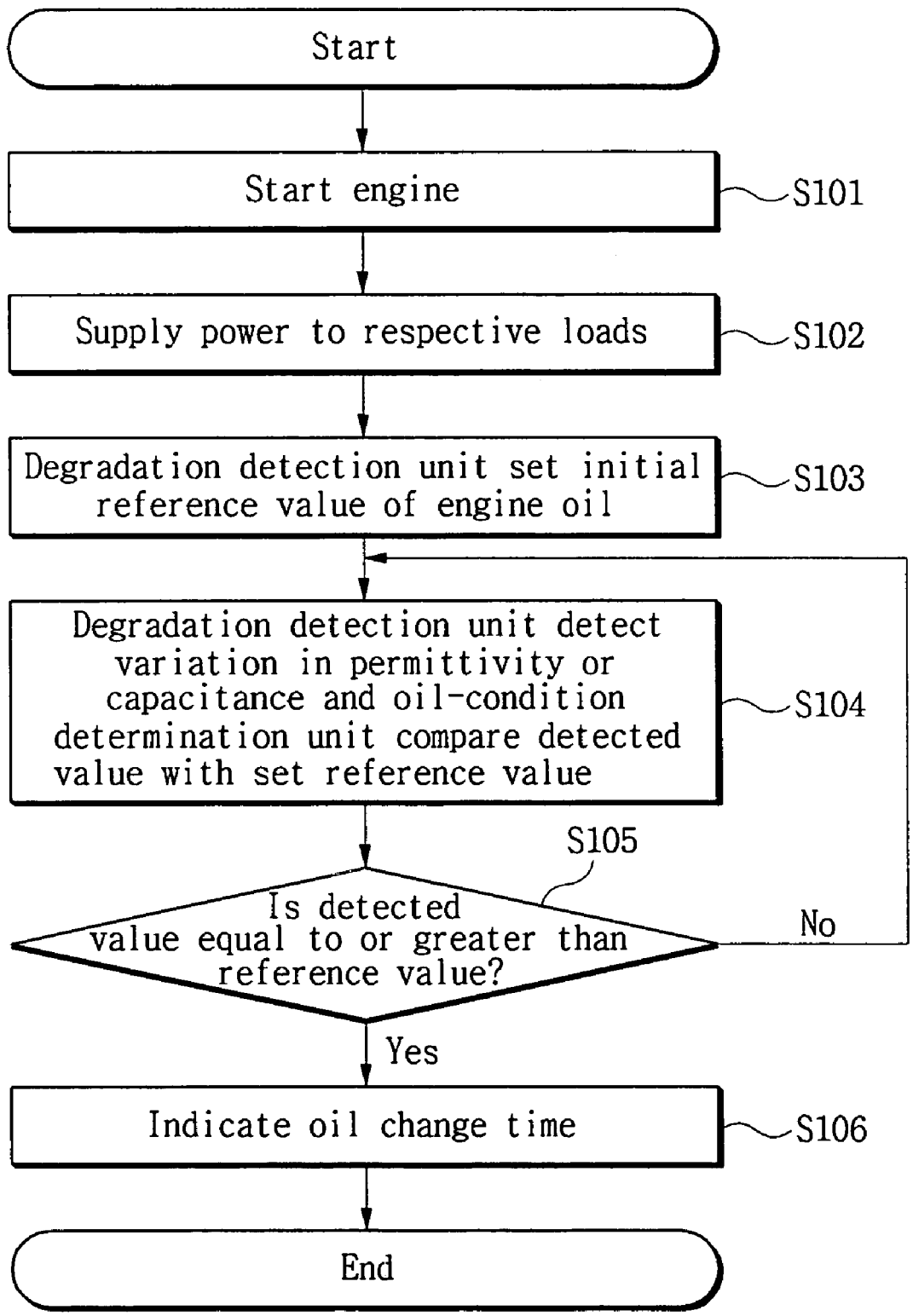
FIG. 9 is a flowchart illustrating a method of determining the time to change automobile engine oil according to the present invention.

FIG. 8 is a block diagram schematically showing the construction of an apparatus for determining the time to change automobile engine oil according to the present invention, and FIG. 9 is a flowchart illustrating a method of determining the time to change automobile engine oil according to the present invention.

Referring to FIG. 8, the apparatus for determining the time to change automobile engine oil according to the present invention includes a power source unit 30 for converting power, which is supplied from a battery 80, into required power and supplying the necessary power at the time of starting, a degradation detection unit 10 installed in an engine oil chamber and using carbon nanotubes as a sensor as detecting the degradation of the engine oil, a drive unit 20 for driving the operation of the degradation detection unit 10 when supplied with power from the power source unit 30 and enabled, a small signal amplification unit 40 for amplifying a minute signal output from the degradation detection unit 10, an oil-condition determination unit 50 for comparing a value, corresponding to the degraded state of the engine oil based on a detection signal transferred from the small signal amplification unit 40, with a set reference value and determining the time to change the engine oil, an amplification unit 60 for amplifying a signal detected and thereby the oil-condition determination unit 50 to a preset level, and a display unit 70 for displaying a signal, which is output from the oil-condition determination unit 50, in text or predetermined form as information about oil change time.

When the automobile starts, the power source unit 30 converts 12V DC power, which is supplied from the battery 80, into the necessary power, which is required by each load, and supplies the necessary power to each load.

The power source unit 30 includes a DC/DC converter 31 for converting 12V DC power, which is supplied from the battery 80, into 15V power, which is required by the small signal amplification unit 40, the oil-condition determination unit 50, the amplification unit 60, and the display unit 70, and 5V power, which is required by the drive unit 20 and the degradation detection unit 10, and a regulator 32 for stabilizing the power converted by the DC/DC converter 31.

Furthermore, when supplied with the 5VDC power from the regulator 32 of the power source unit 30 and enabled, the drive unit 20 drives and controls the operation of the degradation detection unit 30.

The degradation detection unit 10, which is a micro sensor, is installed in the engine oil chamber, and measures variation in permittivity or electric conductivity of the engine oil, which varies according to degradation within the engine oil chamber, and outputs a corresponding minute signal.

In this case, the degradation detection unit 10 uses the electric conductivity sensor shown in FIGS. 1 and 2, in which carbon nanotubes are included as the detection film 12, and any one of the permittivity sensors shown in FIGS. 3 to 7, in which carbon nanotubes are included as the detection film 22.

Furthermore, the electric conductivity sensor, which is a sensor of the degradation detection unit 10, includes electrodes 13 to which DC power is applied through lead wires 14, a detection film 12, which is connected between the electrodes and is formed of carbon nanotubes, which are detection material for detecting the decrease in electric conductivity corresponding to the increase in resistance, and a substrate 13 on which the electrodes 13 and the detection film 12 are mounted.

Furthermore, in the apparatus for determining the time to change engine oil according to the present invention, the electrodes 13 may be formed of carbon nanotubes.

Furthermore, in the apparatus for determining the time to change automobile engine oil according to the present invention, the degradation detection unit 20 includes electrodes 23 to which AC power is applied through lead wires 24, a detection film 22 which is connected to the electrodes and is formed of carbon nanotubes capable of detecting variation in permittivity, and a substrate 21 on which the electrodes 23 and the detection film 22 are mounted.

In the degradation detection unit 10 of the apparatus for determining the time to change engine oil according to the present invention, it is preferred that the electrodes 23 be formed of carbon nanotubes.

Furthermore, in the apparatus for determining the time to change automobile engine oil according to the present invention, it is preferred that the electrode 23 or the detection film 22 be branched in a comb-tooth pattern.

Furthermore, in consideration of floating capacitance, it is preferred that the sensitivity of the degradation detection unit vary according to variation in the deposition area of the carbon nanotubes that cover both the electrodes and the predetermined region of the entire area of the substrate.

When DC voltage is applied to new engine oil accommodated in the engine chamber, electric conductivity is measured and set as an initial reference value, the acidity of the internal composition of the engine oil varies according to the time that the engine oil is used and, thus, the extent of adsorption of ions adsorbed to the carbon nanotubes increases, so the electric conductivity sensor, which uses the carbon nanotubes as detection material, shows characteristics of increasing resistance and decreasing electric conductivity.

The detection apparatus using the electric conductivity sensor that uses the carbon nanotubes as detection material compares a measured value depending on variation in resistance with the previously measured reference value, determines the extent of the degradation of the engine oil, and indicates the time to change the engine oil.

Furthermore, the permittivity sensor, which uses carbon nanotubes as detection electrodes, applies AC voltage, compares a measured capacitance value depending on variation in permittivity of engine oil with an initial reference value, determines the extent of the degradation of the engine oil, and indicates the time to change the engine oil.

Furthermore, in the apparatus for determining the time to change automobile engine oil according to the present invention, the small signal amplification unit 40 amplifies the minute output of the degradation detection unit 10, which uses carbon nanotubes as the detection film, to a preset level, and transfers the amplified signal to the oil-condition determination unit 50.

The oil-condition determination unit 50, which is a micro processor, compares the detected permittivity or electric conductivity of engine oil with the set reference value and determines the extent of the degradation of the engine oil.

In the case where it is determined that a value corresponding to the extent of the degradation is equal to or greater than the set reference value, the oil-condition determination unit 50 determines that the time to change the engine oil is reached and outputs corresponding information.

Furthermore, the amplification unit 60 amplifies a signal, which is provided from the oil-condition determination unit 50, to a preset level, and outputs the amplified signal to the display unit 70.

The small signal amplification unit 40 and the amplification unit 60 may be designed and implemented using OP-amps.

In this case, the apparatus for determining the time to change automobile engine oil according to the present invention may be integrated into a single unit by mounting the power source unit 30, the drive unit 20, the degradation detection unit 10, the small signal amplification unit 40, the oil-condition determination unit 50, and the amplification unit 60 on a single Printed Circuit Board (PCB) 100.

Furthermore, the display unit 70 includes a Light Emitting Diode (LED) lamp or a Liquid Crystal Display (LCD) means in the cluster, and notifies the drive of the time to change the engine oil by displaying information about the time to change the oil, which is provided from the amplification unit 60, in text or predetermined form.

Furthermore, in the apparatus for determining the time to change automobile engine oil according to the present invention, it is preferred that the voltage device_(not shown) of the power source unit 30 further include a thermal sensor that allows power to be applied in a temperature range above 80° C.

Furthermore, in a sensor for measuring variation in permittivity, which is one of the sensors for detecting the time to change automobile engine oil according to the present invention, it is preferred that the power source frequency applied by the drive unit be within a range from 10 KHz to 10 GHz.

It is preferred that the voltage device of the power source unit 30 includes a thermal sensor (not shown) so that power is applied only within a specific temperature range.

That is, the regulator is governed to operate at above 80° C. by the thermal sensor, and the temperature for measuring capacitance is 85° C.

The temperature of the engine oil must be above 80° C. in order to minimize the influence of water on the output of the sensor, because the capacitance value is highly subject to being affected by the water content of engine oil.

Furthermore, in a sensor for measuring variation in permittivity, the frequency of a power source applied by an oscillator (not shown) provided in the drive unit 20 must be within the range from 10 kHz to several GHz.

This is because, in contrast to the reversion of the relative permittivity of oil due to temperature when the capacitance value of the existing sensor is outside a power source frequency from 50 to 500 kHz, carbon nanotubes are appropriate for the measurement of the extent of the degradation over the oil in a full frequency range. However, it cannot detect exact variation due to the influence of Amplitude Modulation (AM) radio frequencies.

The detection process by the apparatus for determining the time to change automobile engine oil according to the present invention, which includes the above-described functions, is described with reference to FIG. 9 below.

First, when engine oil comes into contact with the detection film of the degradation detection unit 10, that is, the carbon nanotubes, in an engine oil chamber, and then the engine of an automobile is started, the operation of various loads provided in the automobile by power supplied from the battery 80 is started at step S101.

At step S102, the DC/DC converter 31 in the power source unit 30 converts a power of 12VDC, which is supplied from the battery 80, into a power of 15V, which is required by the small signal amplification unit 40, the oil-condition determination unit 50, the amplification unit 60, and the display unit 70, and into a power of 5V, which is required by the drive unit 20 and the degradation detection unit 10. Thereafter, the converted powers are stabilized through the regulator 32 and are then supplied to respective loads.

Accordingly, when the drive unit 20 is enabled by the power of 5VDC supplied from the regulator 32 provided in the power and drives the operation of the degradation detection unit 10, the degradation detection unit 10, which is formed of a micro sensor including carbon nanotubes and is installed in the oil chamber, measures the permittivity or electric conductivity of previously injected engine oil and sets an initial reference value at step S103.

Thereafter, when the degradation detection unit 10 detects variation in the permittivity or electric conductivity of the engine oil according to degradation, and corresponding information is amplified by the small signal amplification unit 40 and is then applied to the oil-condition determination unit 50, that is, a microprocessor, the oil-condition determination unit 50 compares the currently detected value with the set reference value to determine the extent to which the engine oil is degraded based on the variation in the permittivity or electric conductivity of the detected engine oil at step S104, and determines whether the measured value is equal to or greater than the set value at step S105.

If, as a result of the determination at step S105, the currently detected value, corresponding to the variation in the permittivity or electric conductivity of the engine oil, is less than the set reference value, it is determined that the current condition of the engine oil is normal, and a return to step S104 is performed. In contrast, if the currently detected value is equal to or greater than the set reference value, it is determined that a time is reached at which the engine oil has degraded beyond a reference level and, thus, that the viscosity of the oil has decreased to an extent at which lubrication of the engine cannot be performed, and corresponding information is output to the amplification unit 60.

Accordingly, the amplification unit 60 amplifies a signal, which is provided from the oil-condition determination unit 50 and indicates that it is time to change the engine oil, and the display unit 70, which includes a lamp or an LCD display means in the cluster, notifies a driver that the time to change the engine oil has been reached by displaying information about the fact in text or in another predetermined form at step S106.

As described above, measurements of (driving distance for engine oil are performed using a sensor comprising carbon nanotubes that function as the detection film.

Figure 10:
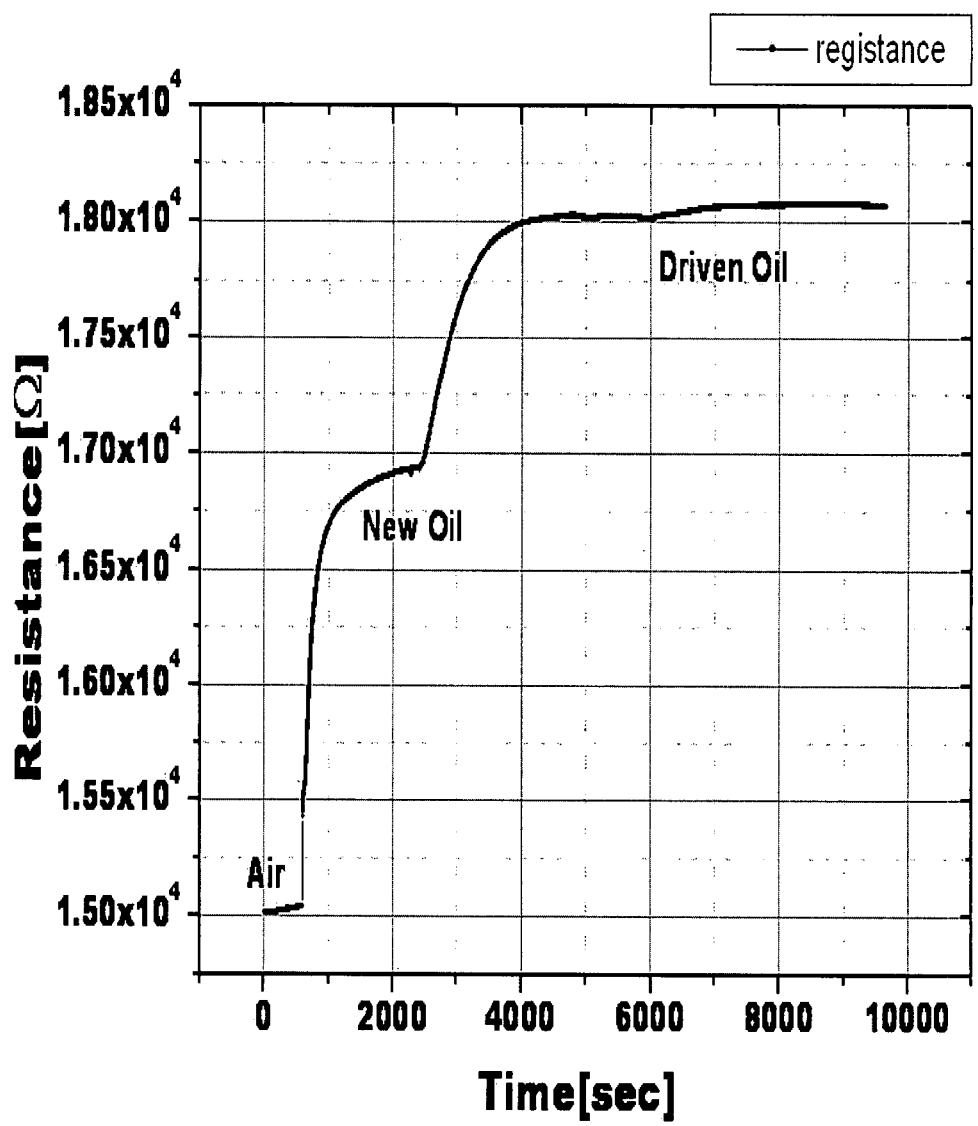
FIG. 10 is a graph showing variation in resistance of engine oil over driving time, as detected by a sensor.
Figure 11:
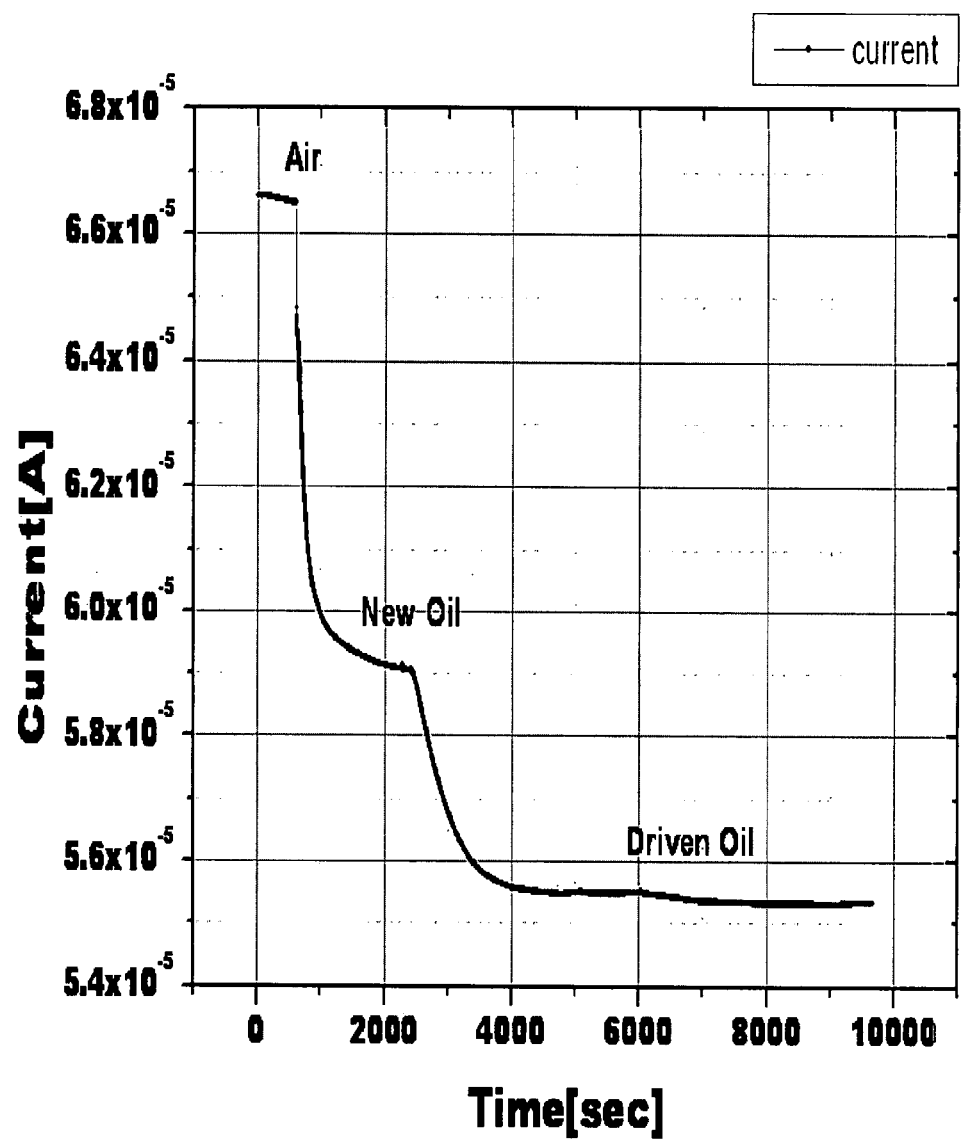
FIG. 11 is a graph showing variation in current in engine oil over driving time, as detected by a sensor.

From FIGS. 10 and 11, it can be seen that the values of current and resistance vary according to driving distance and according to engine oil, and that the sensor and the detection apparatus can measure the degradation of the automobile engine oil based on the variation thereof.

As described above, the present invention measures the time to change engine oil and issues an alarm, so that anybody can easily determine the time to change the engine oil without the help of a skilled inspector, and thus increases a user's convenience.

Furthermore, the present invention enables the engine oil to be changed at an accurate change time, so that an automobile engine can be protected and thus last longer, and unnecessary repair costs can be avoided.

Furthermore, the present invention is advantageous in that environmental pollution can be prevented because the engine oil is changed at the correct time.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for determining a time to change automobile engine oil, comprising:
a power source unit for converting power, which is supplied from a battery, into necessary power and supplying the necessary power at a startup time;
a degradation detection unit installed in an engine oil chamber and formed using carbon nanotubes as a sensor capable of detecting degradation of the engine oil;
a drive unit for driving operation of the degradation detection unit when enabled by power supplied from the power source unit;
a small signal amplification unit for amplifying a minute signal output from the degradation detection unit;
an oil-condition determination unit for comparing a value, corresponding to the degraded state of the engine oil, with a set reference values based on a detection signal transferred from the small signal amplification unit, and thereby determining a time to change the engine oil;
an amplification unit for amplifying a signal detected by the oil-condition determination unit to a preset level; and
a display unit for displaying a signal, which is output from the oil-condition determination unit, in text or predetermined form as information about an oil change time;
wherein the sensor of the degradation detection unit is an electric conductivity sensor, the electric conductivity sensor comprising:

electrodes to which power is applied;

a detection film which is connected to both the electrodes and is formed of carbon nanotubes capable of detecting variation in permittivity; and a substrate on which the electrodes and the detection film are mounted.

2. The apparatus as set forth in claim 1, wherein the electrodes are formed of carbon nanotubes.

3. The apparatus as set forth in claim 1, wherein each of the electrodes is branched in a comb-tooth pattern.

4. The apparatus as set forth in claim 1, wherein a sensitivity of the degradation detection unit varies according to variation in a deposition area of the carbon nanotubes that cover both the electrodes and a predetermined region of an entire area of the substrate.

5. The apparatus as set forth in claim 1, wherein the power source unit comprises:

a Direct Current (DC)/DC converter for converting DC power, which is supplied from the battery, into power required by respective loads; and a regulator for stabilizing the power converted by the DC/DC converter.

6. The apparatus as set forth in claim 1, wherein the display unit comprises a Light Emitting Diode (LED) or Liquid Crystal Display (LCD) device in a cluster.

7. The apparatus as set forth in claim 1, wherein the display unit further comprises an audio speaker for issuing information about oil change time in alarm sound or voice message form.

8. The apparatus as set forth in claim 1, wherein a voltage device of the power source unit further comprises a thermal sensor so that power can be applied in a temperature range above 80° C.

9. The apparatus as set forth in claim 1, wherein a power source frequency applied by the drive unit is within a range from 10 kHz to 10 GHz.

* * * * *